(12) United States Patent
Kameo et al.

(10) Patent No.: US 8,075,541 B2
(45) Date of Patent: Dec. 13, 2011

(54) ABSORBENT ARTICLE INCLUDING REAR WING PORTIONS

(75) Inventors: Yoji Kameo, Tochigi-ken (JP); Tetsuya Kusagawa, Tochigi-ken (JP); Mitsugu Hamajima, Tochigi-ken (JP)

(73) Assignee: Kao Corporation, Tokyo (JP)

( * ) Notice: Subject to any disclaimer, the term of this patent is extended or adjusted under 35 U.S.C. 154(b) by 113 days.

(21) Appl. No.: 11/594,186

(22) Filed: Nov. 8, 2006

(65) Prior Publication Data

US 2007/0055212 A1    Mar. 8, 2007

Related U.S. Application Data

(62) Division of application No. 09/472,972, filed on Dec. 28, 1999, now abandoned.

(30) Foreign Application Priority Data

Dec. 28, 1998   (JP) .................................... 10-372065
Dec. 28, 1998   (JP) .................................... 10-372066

(51) Int. Cl.
  *A61F 13/15*   (2006.01)
  *A61F 13/20*   (2006.01)
(52) U.S. Cl. .......................... 604/385.04; 604/385.01
(58) Field of Classification Search .................. 604/380, 604/385.01–385.05
  See application file for complete search history.

(56) References Cited

U.S. PATENT DOCUMENTS

| | | | |
|---|---|---|---|
| 3,954,107 A | 5/1976 | Chesky et al. | |
| 4,079,739 A | 3/1978 | Whitehead | |
| 4,321,924 A * | 3/1982 | Ahr | 604/378 |
| 4,589,283 A | 5/1986 | Morrison, Jr. | |
| 4,589,876 A | 5/1986 | Van Tilburg | |
| 4,687,478 A | 8/1987 | Van Tilburg | |
| 5,092,860 A | 3/1992 | Pigneul et al. | |
| 5,267,992 A | 12/1993 | Van Tilburg | |
| 5,275,591 A | 1/1994 | Mavinkurve | |
| 5,374,260 A | 12/1994 | Lemay et al. | |
| 5,423,786 A | 6/1995 | Fung et al. | |
| 5,447,507 A | 9/1995 | Yamamoto et al. | |
| 5,466,232 A | 11/1995 | Cadieux et al. | |
| 5,489,283 A | 2/1996 | Van Tillburg | |
| 5,490,847 A | 2/1996 | Correa et al. | |
| H1585 H | 8/1996 | Ahr | |
| 5,578,025 A * | 11/1996 | May | 604/385.31 |
| 5,591,148 A | 1/1997 | McFall et al. | |

(Continued)

FOREIGN PATENT DOCUMENTS

GB   2 276 552   10/1994

(Continued)

*Primary Examiner* — Michele M Kidwell
(74) *Attorney, Agent, or Firm* — Birch, Stewart, Kolasch & Birch, LLP

(57) ABSTRACT

An absorbent article includes an elongate absorbent body and a pair of left and right rear wing portions disposed at longitudinal opposite left and right sides of the absorbent body in a rear zone thereof. Each of the rear wing portions includes a liquid-retentive wing absorbent core. Furthermore, an absorbent article includes an elongate absorbent body and a pair of left and right wing portions disposed at longitudinal opposite left and right sides of the absorbent body. Each of the wing portions includes a laminated sheet formed by laminating at least two sheet materials and the two sheets of material are bonded to and along opposite side edges of the absorbent body with an adhesive agent except for non-coated linear areas of a predetermined width formed on the wing portions.

14 Claims, 3 Drawing Sheets

U.S. PATENT DOCUMENTS

| | | |
|---|---|---|
| 5,613,959 A | 3/1997 | Roessler et al. |
| 5,722,966 A | 3/1998 | Christon et al. |
| 5,797,894 A | 8/1998 | Cadieux et al. |
| 5,868,725 A | 2/1999 | Coles et al. |
| 5,895,379 A | 4/1999 | Litchholt et al. |
| 6,004,893 A | 12/1999 | Van Tilburg |
| 6,159,190 A | 12/2000 | Tanaka et al. |
| 6,159,191 A | 12/2000 | Mishima et al. |
| 6,175,056 B1 | 1/2001 | Carlucci et al. |
| 6,746,435 B1 | 6/2004 | Van Tilburg |

FOREIGN PATENT DOCUMENTS

| | | |
|---|---|---|
| WO | WO-98/25561 | 6/1998 |
| WO | 98/42285 | * 10/1998 |

* cited by examiner

ABSORBENT ARTICLE INCLUDING REAR WING PORTIONS

This application is a Divisional of application Ser. No. 09/472,972, filed Dec. 28, 1999, now abandoned; which claims priority of Japanese Application Nos. 10-372065 and 10-372066, both filed on Dec. 28, 1998, the content of which is disclosed below in its entirety.

BACKGROUND OF THE INVENTION

1. Field of the Invention

The present invention relates to an absorbent article which is superior in leakage preventing performance from the rear of the article.

Also, the present invention relates to an absorbent article which is superior in leakage preventing performance and in handling performance.

2. Description of the Related Art

Various types of absorbent articles are proposed each having a pair of left and right wing portions at a front zone or a rear zone thereof, etc. for enhancement of leakage preventing performance.

Conventional backwardly located wing portions are designed to prevent leakage in such a manner as to intercept body fluids which have overflowed from an absorbent core at a rear zone or which have exuded along a topsheet of the absorbent article. However, an absorbent article with wing portions having the above mentioned functions is not sufficient in leakage preventing effect.

The conventional absorbent articles with a pair of left and right wing portions are packaged and sold in a condition such that the wing portions are folded towards a skin contacting surface side or a skin non-contacting surface side. However, it is not an easy job to fold the wing portions. Moreover, since a permanent fold is formed on the wing portions when they are taken out of packages, handling performance is inferior.

SUMMARY OF THE INVENTION

It is, therefore, a first object of the present invention to provide an absorbent article which is superior in leakage preventing performance, in particular from the rear portion.

It is a second object of the present invention to provide an absorbent article which is superior in leakage preventing performance and which is favorable in handling performance.

The present invention (first invention) has achieved the first object by providing an absorbent article comprising an elongate absorbent body and a pair of left and right rear wing portions disposed at longitudinal opposite left and right sides of the absorbent body in a rear zone thereof, wherein each of the rear wing portions includes a liquid-retentive wing portion absorbent core.

The present invention (second invention) has achieved the second object by providing an absorbent article comprising an elongate absorbent body and a pair of left and right wing portions disposed at longitudinal opposite left and right sides of the absorbent body, wherein each of the wing portions is formed by laminating at least two sheet materials and the two sheet materials are bonded through an adhesive agent only excluding adhesive agent non-coated areas of a predetermined width formed on the wing portions along opposite side edges of the absorbent body.

The absorbent article according to the present invention (first invention) is superior in leakage preventing performance, in particular from the rear portion of the article.

The absorbent article according to the present invention (second invention) is superior in leakage preventing performance and excellent in handling performance.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings, which are given by way of illustration only, and thus are not limitative of the present invention, and wherein.

DETAILED DESCRIPTION OF THE INVENTION

One preferred embodiment of the present invention (first invention) will now be described.

Figure 1:
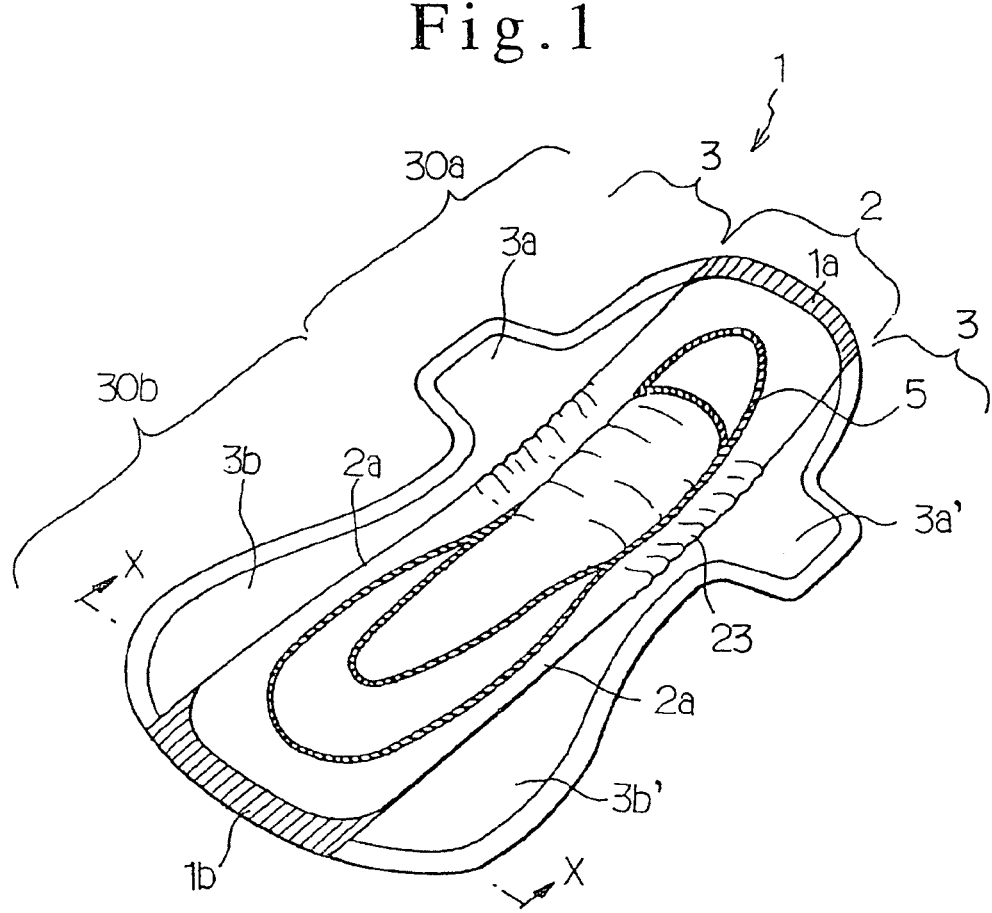
FIG. 1 is a perspective view showing one embodiment of an absorbent article according to the present invention (first invention)
Figure 2:
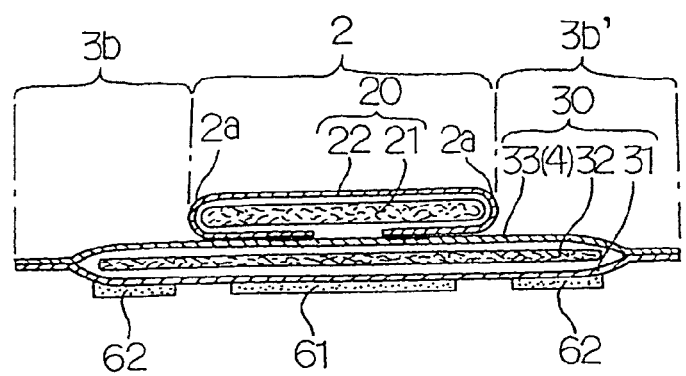
FIG. 2 is a sectional view taken on line X-X of FIG. 1.

A sanitary napkin 1 as an absorbent article according to this embodiment comprises, as shown in FIGS. 1 and 2, an elongate absorbent body 2 and a pair of left and right rear wing portions 3b, 3b' disposed at longitudinal opposite left and right sides in a rear zone of the absorbent body 2.

In the sanitary napkin 1 according to this embodiment, each of the rear wing portions 3b, 3b' includes a liquid-retentive wing portion absorbent core 32.

This will be described in more detail. The absorbent body 2 includes a liquid-retentive body absorbent core 21. The body absorbent core 21 and each wing portion absorbent core 32 are isolated from each other through an isolating member 4. That is, the body absorbent core 21 and each wing portion absorbent core 32 are designed such that they are not directly contacted with each other. By virtue of the isolating member 4 between the body absorbent core 21 and each wing portion absorbent core 32, a large quantity of fluid is prevented from being absorbed by the wing portion absorbent cores at a time and the absorptive force of the wing portion absorbent cores 32 is sustained in a favorable condition during use.

Specifically, the sanitary napkin 1 according to this embodiment comprises, in its width direction, an elongate upper layer portion 20 comprised of the body absorbent core 21 and a liquid-permeable topsheet 22 disposed in such a manner as to cover its upper and side surfaces; and a lower layer portion 30 comprised of a liquid-impermeable antileakage sheet 31, a liquid-permeable sheet 33 having a generally same configuration as the antileakage sheet 31 and the wing portion absorbent cores 32 interposed between the sheets 31 and 33. A rear zone 30b side and a front zone 30a side of the lower layer portion 30 are enlarged in width dimension. The upper layer portion 20 is fixed onto the liquid-permeable sheet 33 of the lower layer portion 30 through an adhesive agent such that the longitudinal opposite side portions of the lower layer portion 30, which are enlarged in width dimension at the front and rear zones 30a, 30b side, may extend from a longitudinal side edge (side edge 2a of the absorbent body) of the upper layer portion 20. The rear wing portions 3b, 3b' are formed of the extended lower layer portion 30. That is, in this embodiment, the isolating member 4 is formed by the liquid-permeable sheet 33.

The topsheet 22 covers generally the entire surface of the body absorbent core 21, only excluding a central area of the back surface side. The topsheet 22 is fixed at a widthwise generally central area thereof to the liquid-permeable sheet 33 through an adhesive agent. Opposite left and right side edges of the upper layer portion 20 serve as free edge portions 23 which are not fixed to the lower layer portion 30. At the longitudinal opposite edge portions 1a, 1b of the sanitary napkin 1, neither the upper layer portion 20 nor the lower layer portion 30 is provided with an absorbent core, and the upper layer portion 20 is comprised of only the topsheet 22 while the lower layer portion 30 is comprised of only the antileakage sheet 31 and liquid-impermeable sheet 33, both the upper and lower layer portions 20, 30 being integrally heat sealed.

At a skin contactable portion which is located at the front zone side and which is, when in wear, contacting with the liquid-discharging portion of the wearer, an elastic member is disposed on an edge end portion of each free edge portion 23 (not shown). Instead, a gather is formed thereon. At the skin contactable portion, the body absorbent core 21 is bulky. A groove 5 is formed in the upper layer portion 20 in the same manner as in the common sanitary napkins.

The sanitary napkin 1 according to this embodiment includes a pair of left and right front wing portions 3a, 3a' which are disposed at the longitudinal opposite left and right sides of the absorbent body 2 on the front zone side. Each of the front wing portions 3a, 3a' includes a wing portion absorbent core 32. That is, the lower layer portion 30 is provided, on the front zone 30a side which is located on the longitudinal second end portion side, with a portion whose longitudinal side edges extend outwardly. The front wing portions 3a, 3a' are formed by such extended portions.

The term "front zone" used herein refers to an area or zone of the absorbent article located on the front side of the wearer when in use and more specifically, it refers to an area of the absorbent article located forwardly of the central portion in the longitudinal direction of the absorbent article. Similarly, the term "rear zone" used herein refers to an area or zone of the absorbent article located on the rear side of the wearer when in use and more specifically, it refers to an area of the absorbent article located backwardly of the central portion in the longitudinal direction of the absorbent article.

On the side of back surfaces each of the absorbent body 2, front wing portions 3a, 3a' and rear wing portions 3b, 3b', namely, on an undergarment attachment surface of the antileakage sheet, those surfaces are provided with a body adhesive area 61 for the attachment of an adjacent undergarment, front wing adhesive areas (not shown) and rear wing adhesive areas 62, respectively.

The material for forming the respective component members in the sanitary napkin according to this embodiment will now be described.

As the topsheet 22 and the antileakage sheet 31, a liquid-permeable sheet and a liquid-impermeable sheet commonly used for sanitary napkins can be used without any limitation, in particular.

As the liquid-permeable sheet 33 as the isolating member 4, a nonwoven fabric formed of polyethylene (PE) fiber, polypropylene (PP) fiber, polyethylene-terephthalate (PET) fiber, PE/PET composite fiber or the like. or a sheet material such as polyolefine perforated film, etc. formed by perforating a sheet of film such a polyethylene or the like is used.

The isolating member 4 is preferably formed of material capable of restraining absorption so that body fluids once absorbed by the body absorbent core 21 will not immediately migrate into the wing portion absorbent cores 32. That is, it is preferred that the isolating member 4 is more lowered in capillary penetration pressure than the absorptive material used for the body absorbent core 21, more lowered in hydrophilic property than the body absorbent core 21 and more increased in average pore size than the body absorbent core 21.

In the where the isolating member 4 is a liquid-impermeable sheet such as a polyethylene film, only the back surface side of the body absorbent core 21 is used so that the wing portion absorbent core 32 can absorb body fluids.

As the absorbent core 21, one used for sanitary napkins can be used without any limitation in particular.

The wing portion absorbent cores 32 are preferably formed of a sheet-like material having reduced liquid dispersibility. Specifically, a dry type pulp sheet obtained by piling up pulp fibers and fixing them with a chemical binder, an embossed absorption paper obtained by embossing a wet type absorption paper, etc. can be listed. Among them, the embossed absorption paper is particularly preferable in view of cost.

The wing portion absorbent cores 32 have a somewhat supplementary function in which they absorb body fluids exuded from the body absorbent core 21. With respect to dispersibility at the time of absorption, reduced dispersibility is preferred. Specifically, under the conditions of temperature of 20° C. and humidity of 65%, after dropping of 1 g of physiological solution of sodium chloride from about 1 cm above the wing portion absorbent core, the absorption area is preferably 80 $cm^2$ or less after the passage of one minute of time and more preferably 50 $cm^2$ or less. By making the absorption area 80 $cm^2$ or less, dispersion of liquid can be delayed, thus enabling to prevent the body fluids from dispersing within the wing portion absorbent core and leaking therefrom.

The embossed absorption paper is enlarged in thickness by subjecting an absorption paper to embossing treatment, so that liquid will not disperse in one direction. The embossing pattern is not limited in particular. However, the absorption paper is preferably embossed in a dotted pattern at density of 1 to 30 dots/$cm^2$ per 1 $cm^2$.

With respect to the hardness of the wing portion absorbent core 32, in view of twist prevention and wearing feeling, the wing portion absorbent core 32 is preferably 20 to 500 g in buckling strength and more preferably 50 to 300 g. By making the buckling strength 20 g or more, the wing portions do not get twisted easily and by making the buckling strength 500 g or less, it is prevented that the entire wing portion absorbent core 32 gets overly stiffened. Owing to this arrangement, the wearer can be free from foreign feel when the absorbent article is in wear.

The buckling strength can be measured in the following manner.

<Measuring Method>

Measurement of the buckling strength is carried out using an absorbent core, which was left for a day or more in the environment of 20 degrees Centigrade and 65% of relative humidity (RH), under the same conditions of temperature and humidity.

Specifically, an absorbent core is cut out having a length of 150 mm and a width of 30 mm and served as a specimen. Longitudinal ends of this specimen are overlapped into a loop-like configuration such that the width of the overlapped portion is 5 mm. Then, upper and lower areas of 1 cm of the loop-like specimen are fastened at two spots by a stapler with the direction of a length of its needle held in orthogonal to the compressing direction. By doing so, a ring-shaped sample is obtained. The obtained sample is placed on a specimen table of a Tensilon tester (merchandise name: "RTM-25" manufactured by TOYO BALDWIN Co., Ltd.) with its longitudinal direction serving as a lower surface. After placement, the specimen is compressed in a compression test mode at a measuring speed of 10 mm/min. to obtain a maximum strength when the specimen is buckled. The measuring is carried out in the same manner with respect to five samples separately prepared and an average is obtained so as to be served as a buckling strength.

In order to obtain a desired stiffness and dispersibility, the thickness of each wing portion absorbent core 32 is preferably 0.2 to 3 mm under a load of 2.5 g/cm$^2$ and more preferably, 0.3 to 2 mm.

As a preferable wing portion absorbent core, a dry type pulp sheet (merchandise name: "JS-50HB" manufactured by HAVIX Co. Ltd., or others) an embossed absorption paper obtained by embossing a wet type absorption paper, and the like can be listed. Among them, the embossed absorption paper is more preferable in view of cost.

The sanitary napkin 1 as an absorbent article according to this embodiment can be used in the same manner as the common nighttime sanitary napkins.

Since the sanitary napkin 1 according to this embodiment is constructed in the manner as mentioned above, the fluids which have exuded from a rear region of the absorbent body and the fluids which flow without having been absorbed can effectively be absorbed by the rear wing portions 3b, 3b'. Accordingly, it is superior in leakage preventing performance from the rear region of the napkin 1.

Especially, in the case where the wing portion absorbent cores 32 are formed of a sheet-like material having reduced liquid dispersibility, it is seldom that the absorptive capability of the entire surface of each wing portion absorbent core is fully used up because the fluids once absorbed are hardly dispersed. Thus, a state is maintained in which some part of the entire surface has the absorptive capability. Therefore, leakage of fluids caused by not having been absorbed can effectively be prevented.

The sanitary napkin according to this embodiment can be obtained as follows. First, the wing portion absorbent cores are placed on the antileakage sheet, then the liquid-permeable sheet is additionally placed thereon in such a manner as to cover the wing portion absorbent cores, and the antileakage sheet and the liquid-permeable sheet are fixedly heat sealed at a peripheral edge portion of each wing portion absorbent core to thereby form the lower layer portion. Then, the upper layer portion, which has been separately formed by covering the body absorbent core with the topsheet, is affixed onto the lower layer portion through an adhesive agent and the longitudinal opposite end portions are heat sealed, for example.

Figure 3:
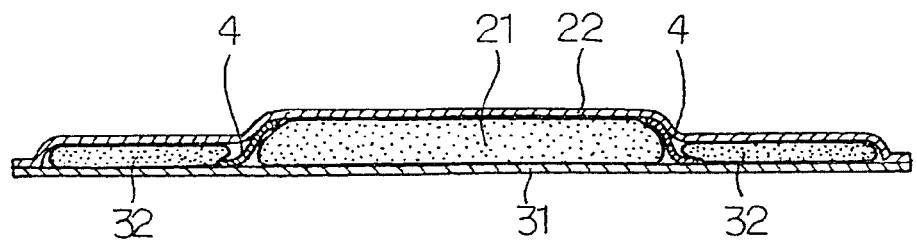
FIG. 3 is a widthwise sectional view (corresponding to FIG. 2) showing another embodiment of the absorbent article according to the present invention (first invention)

In the above embodiment, a sanitary napkin comprised of the upper layer portion 20 and the lower layer portion 30 has been exemplified. In the alternative, the sanitary napkin may be constructed such that the body absorbent core 21 and the wing portion absorbent cores 32 are arranged in parallel in a width direction of the sanitary napkin as shown in FIG. 3 and a sheet material formed of a hydrophobic nonwoven fabric, a foam or the like is disposed between the body absorbent core 21 and each wing portion absorbent core 32 as the isolating member 4.

One embodiment of the second invention will now be described. In the following description, different points from the first invention will be described in great detail and description of the same points will be omitted. For those points not described in particular, the description made with respect to the embodiment of the first invention is applicable, where appropriate.

Figure 4:
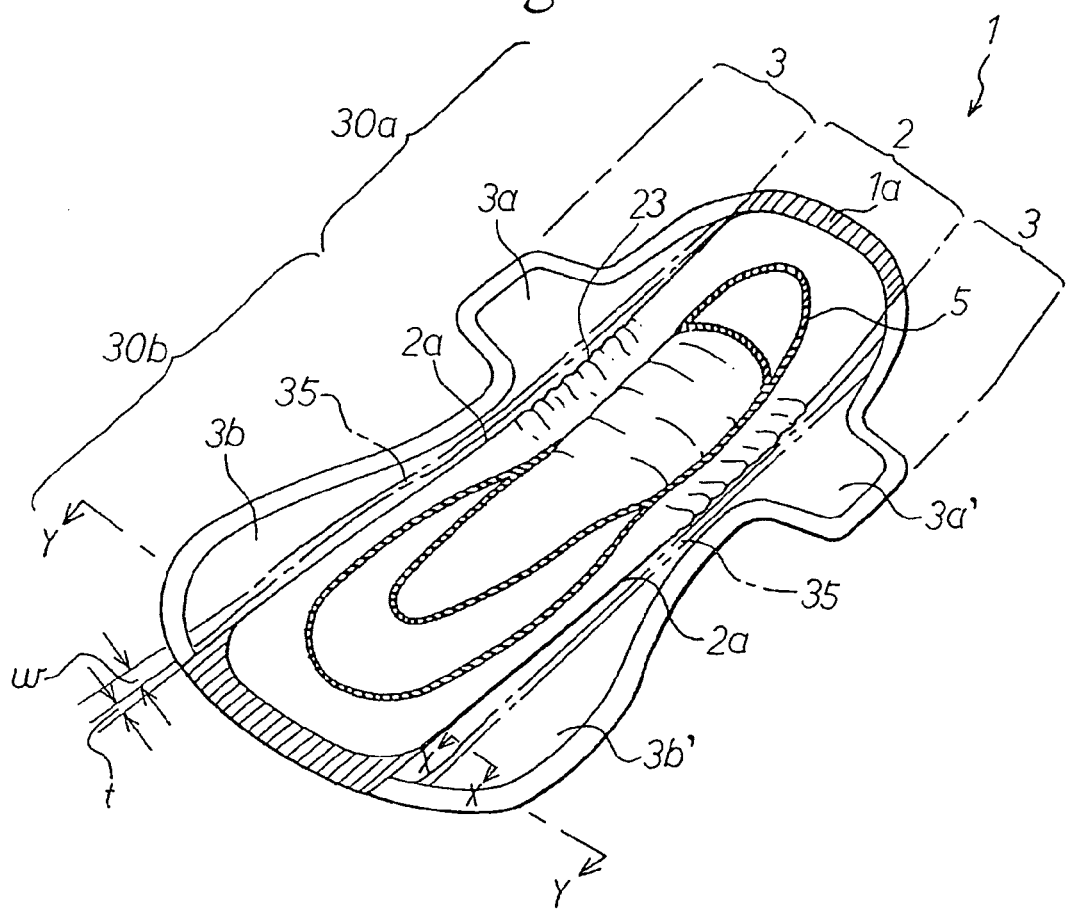
FIG. 4 is a perspective view showing one embodiment of an absorbent article according to the present invention (second invention)
Figure 5:
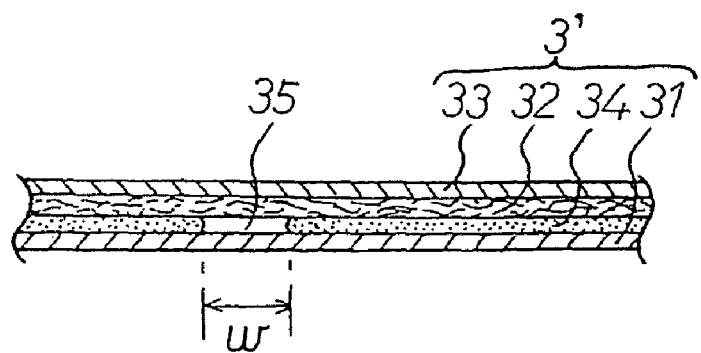
FIG. 5 is an enlarged sectional view taken on line X-X of FIG. 4.
Figure 6:
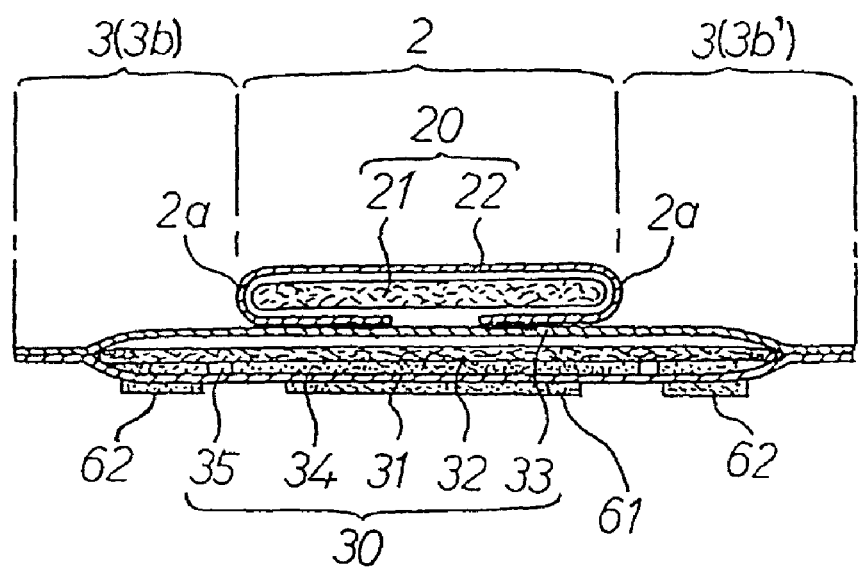
FIG. 6 is a sectional view schematically showing a Y-Y section of FIG. 4.

A sanitary napkin 1, as an absorbent article according to one embodiment of the second invention, has a pair of wing portions 3 each formed of a laminated sheet 3' by laminating at least two sheet materials as shown in FIGS. 4 to 6. The two sheet materials are bonded through an adhesive agent 34 except for linear non-coated areas 35 of a predetermined width formed on the wing portions 3 along opposite side edges 2a of the absorbent body 2.

This will be described in more detail. The two sheet materials are; an antileakage sheet 31 and an absorptive sheet 32 disposed on the antileakage sheet 31. In this embodiment, the laminated sheet 3' further includes a liquid-permeable sheet 33 disposed in such a manner as to cover an upper surface side of the absorptive sheet 32. According to the arrangement of the liquid-permeable sheet thus disposed, blood which flows to the rear side portion of the napkin can promptly permeates through the liquid-permeable sheet and can be absorbed by the absorptive sheet, blood is prevented from leaking, and no blood remains in the liquid-permeable sheet, so that excellent dry feeling is exhibited.

The wing portions 3 comprise a pair of left and right front wing portions 3a, 3a' disposed at longitudinal opposite left and right sides of the absorbent body 2 on the side of a front zone thereof and a pair of left and right rear wing portions 3b, 3b' disposed at longitudinal opposite left and right sides of the absorbent body 2 on the side of a rear zone thereof. This arrangement makes it possible that, in use, the front wing portions is wrapped around the shorts thereby preventing the napkin from twisting and blood from leaking to the shorts, and that the rear wing portions cover the shorts in the wider range thereby preventing blood from leaking to the rear side.

The sanitary napkin 1 according to this embodiment comprises, in its width direction, an elongate upper layer portion 20 comprised of a body absorbent core 21 and a liquid-permeable topsheet 22 disposed in such a manner as to cover its upper and side surfaces; and a lower layer portion 30 comprised of a liquid-impermeable antileakage sheet 31, a liquid-permeable sheet 33 having a generally same configuration as the antileakage sheet 31 and the absorptive sheet 32 interposed between the sheets 31 and 33. A rear zone 30b side and a front zone 30a side of the lower layer portion 30 are enlarged in width dimension.

The upper layer portion 20 is placed on the liquid-permeable sheet 33 of the lower layer portion 30 such that the longitudinal opposite side portions of the lower layer portion 30, which are enlarged in width dimension may extend from longitudinal side edges of the upper layer portion 20. The front wing portions 3a, 3a' and the rear wing portions 3b, 3b' are formed by the extended lower layer portion 30.

According to the arrangement of the upper layer portion 20 and the lower layer portion 30 thus structured, the lower layer portion 30 firmly fixes to the shorts and the upper layer portion 20 fits to the body, so that blood is easy to absorb and hard to leak. In addition, even if the lower layer portion twists in consistent with the twist of the shorts, the upper layer portion is free from the twist. Also, even if the upper layer portion twists, the lower layer portion keeps from twisting, thus providing a more hardly-leaking structure.

In this embodiment, an adhesive agent 34 is applied to an entire surface of the absorptive sheet 32 except for linear non-coated areas 35, so that the antileakage sheet 31 and the absorptive sheet 32 are bonded together. The non-coated areas 35 are provided on the absorbent body 2 side in the front wing portions 3$a$, 3$a'$ and the rear wing portions 3$b$, 3$b'$. In this way, it is desirable, in view of operability, to provide non-coated areas at locations adjacent to the absorbent body 2. A distance t from a side edge 2$a$ to the absorbent body 2 is preferably 0 to 40 mm and more preferably 0 to 20 mm. That is, in the case where there are provided an upper layer portion and a lower layer portion as in this embodiment, the side edge 2$a$ of the absorbent body 2 may be located on the non-coated area 35.

A predetermined width w of the adhesive agent non-coated area 35 is preferably 2 to 20 mm in view of handling performance of the wing portion when attached to the adjacent undergarment.

Also, in view of handing performance of the wing portion, the coating basis weight of the adhesive agent 34 is preferably 3 to 400 g/m$^2$ and the coating thickness is preferably 3 to 400 µm.

The bending stiffness of the adhesive agent coated area is preferably 1.2 times or more and particularly preferably 1.5 times or more of the bending stiffness of the adhesive agent non-coated area 35. By making the bending stiffness of the adhesive agent coated area 1.2 times or more of the bending stiffness of the adhesive agent non-coated area 35, a difference of handling performance occurs due to a difference in bending stiffness and the wing portion becomes easy to be bent at the adhesive agent non-coated area with the result that the handling performance is enhanced.

The bending stiffness of the adhesive agent non-coated area 35 is preferably 0.0001 to 0.0015 mN·m$^2$/m.

The stiffness of the adhesive agent coated area is preferably 0.002 to 0.02 mN·m$^2$/m.

Recoverability of the adhesive agent non-coated area 35 is preferably 0.05 to 0.15 mN·m/m.

Recoverability of the adhesive agent coated area is preferably 0.18 to 0.5 mN·m/m.

Bending stiffness and recoverability can be measured in the following manner.

The wing portion (which may include the absorbent body where necessary) is cut out having a length of 20 mm and a width of 60 mm, in such a manner as to transverse the adhesive agent non-coated area and served as a sample of the adhesive agent non-coated area. The obtained sample is loaded on a bending stiffness tester (merchandise name: "KES" manufactured by KATO TECH. Co., Ltd.) with its adhesive agent non-coated area located between chucks, and bending stiffness and recoverability are measured.

The adhesive agent coated area is cut out having a length 20 mm and a width 60 mm, so as not to include the adhesive agent non-coated area and served as a sample. The obtained sample is loaded on a bending stiffness tester (merchandise name: "KES" manufactured by KATO TECH. Co., Ltd.), and bending stiffness and recoverability are measured.

The measurement is carried out by bending the entire sample into an arcuate configuration having a constant curvature at a constant velocity and detecting a bending moment resulting therefrom.

The measuring conditions are set such that the deformation speed is 0.5 (cm$^{-1}$)/sec. in a range of the curvature K=−2.5 to +2.5 (cm$^{-1}$).

The bending stiffness is obtained by obtaining an inclination between K=0.5 and K=1.5 from the characteristic observed during the increasing process of an absolute value K. The recoverability is an average value of a hysteresis width in a range of K=0.5 to 1.5.

A basic construction of the absorbent body 2 and the material for forming the topsheet 22, body absorbent core 21, antileakage sheet 31 and liquid-permeable sheet 33 are the same as the embodiment of the first invention.

As the material for forming the absorptive sheet 32, the same material as the material for forming the wing portion absorbent core in the embodiment of the first invention can be used. And the thickness and buckling strength are also preferably the same.

The sanitary napkin 1 as an absorbent article according to this embodiment is sold in the state the front wing portions 3$a$, 3$a'$ and the rear wing portions 3$b$, 3$b'$ are folded towards the skin-contacting surface side or the skin non-contacting surface side of the napkin, respectively, to form a three-fold design and then wrapped up in a package as in the common nighttime sanitary napkins.

With respect to the sanitary napkin of this embodiment, since the non-coated area 35 functions as a flexible axis, the wing portions can easily be to folded when the napkin is wrapped up in a package. Moreover, handling performance is good in use. The wing portions 3 are easy to fold due to the function of the non-coated areas 35 and a permanent fold is not easily formed, either. Accordingly, it can be attached to the adjacent undergarment in a more stable manner, thus further enhancing slip preventing performance and absorbing performance.

In the case where the wing portion uses an absorptive sheet and the absorptive sheet uses an embossed absorption paper, the absorbing performance is more enhanced and the antileakage effect is further enhanced.

The sanitary napkin according to this embodiment can be manufactured in the same manner as the embodiment according to the first invention only except that an adhesive agent is applied to the entire surface of the antileakage sheet only excluding the adhesive agent non-coated area and the absorptive sheet is bonded to the antileakage sheet through the adhesive agent.

Although a sanitary napkin comprised of an upper layer portion and a lower layer portion is exemplified in this embodiment, the body absorbent core and the wing portion absorbent cores may be arranged in parallel in the width direction of the absorbent article.

Although a wing portion comprised of a front and a rear wing portion is exemplified in this embodiment, the wing portion may be comprised of one of the front and rear wing portions.

The configuration of the adhesive agent non-coated area is not limited to the above embodiment. It is also accepted that the adhesive agent non-coated area exhibits a curved configuration, that a plurality of adhesive agent non-coated areas are discontinuously arranged, and that the adhesive agent non-coated areas are arranged in two or more rows in parallel relation.

The adhesive agent applied to the entire surface of the wing portion only excluding the adhesive agent non-coated area, may be applied without leaving any non-coated area, or it may be applied in a spiral pattern or in a line-like pattern.

The two sheet materials forming the wing portion are not necessarily be the absorbent sheet. Instead, the topsheet may be directly extended and laminated on the antileakage sheet Although a sanitary napkin is exemplified in the embodiments according to the first and second inventions, the present invention is likewise applicable to an incontinence pad and the like.

What is claimed is:

1. A sanitary napkin comprising an elongate absorbent body and a pair of left and right rear wing portions disposed at longitudinal opposite left and right sides of said absorbent body in a rear zone thereof, wherein each of said rear wing portions includes a liquid-retentive wing portion absorbent core between a liquid permeable sheet and a liquid impermeable sheet, said left and right rear wing portions located at the rear side of the wearer when worn, said left and right wear wing portions being asymmetrical with regard to a center line which divides the longitudinal length of the absorbent body into halves, and back surfaces of each of said absorbent body and rear wing portions provided with a body adhesive area, and rear wing adhesive area, respectively, wherein each of the wing portion absorbent cores comprises a dry type pulp sheet having reduced liquid dispersibility, wherein there is no step between the back surface of the absorbent body and the back surface of the rear wing portions, wherein said absorbent body includes a liquid-retentive body absorbent core, and wherein said body absorbent core and said wing portion absorbent core are isolated from each other through a liquid permeable isolating member, and wherein the hardness of each of the wing portion absorbent cores is 20 to 500 g in terms of buckling strength.

2. A sanitary napkin according to claim 1, wherein said wing portion absorbent core is 80 cm$^2$ or less in absorptive area after 1 minute after dropping of 1 g of a physiological solution of sodium chloride.

3. A sanitary napkin according to claim 1, wherein said wing portion absorbent core is 20 to 500 g in buckling strength.

4. A sanitary napkin comprising an elongate absorbent body and a pair of left and right wing portions disposed at longitudinal opposite left and right sides of said absorbent body, wherein each of said wing portions includes a liquid-retentive absorbent core and is formed by laminating at least two sheet materials and said two sheet materials are bonded through an adhesive agent only excluding adhesive agent non-coated areas of a predetermined width formed on said wing portions along opposite side edges of said absorbent body, said left and right rear wing portions located at the rear side of the wearer when worn, said left and right rear wing portions being asymmetrical with regard to a center line which divides the longitudinal length of the absorbent body into halves, and back surfaces of each of said absorbent body and rear wing portions provided with a body adhesive area, and rear wing adhesive area, respectively, wherein each of the wing portion absorbent cores comprises a dry type pulp sheet having reduced liquid dispersibility, wherein there is no step between the back surface of the absorbent body and the back surface of the rear wing portions, wherein said absorbent body includes a liquid-retentive body absorbent core, and wherein said body absorbent core and said wing portion absorbent core are isolated from each other through a liquid permeable isolating member, and wherein the hardness of each of the wing portion absorbent cores is 20 to 500 g in terms of buckling strength.

5. A sanitary napkin according to claim 4, wherein said two sheet materials are an antileakage sheet and an absorptive sheet placed on said antileakage sheet.

6. A sanitary napkin according to claim 5, wherein said absorptive sheet is provided on an upper surface side thereof with a liquid-permeable sheet in such a manner as to cover said absorptive sheet.

7. A sanitary napkin according to claim 4, wherein said wing portion comprises a pair of left and right front wing portions disposed at longitudinal opposite left and right sides of said absorbent body on the side of a front zone thereof and a pair of left and right rear wing portions disposed at longitudinal opposite left and right sides of said absorbent body on the side of a rear zone thereof.

8. A sanitary napkin according to claim 5, wherein said wing portion comprises a pair of left and right front wing portions disposed at longitudinal opposite left and right sides of said absorbent body on the side of a front zone thereof and a pair of left and right rear wing portions disposed at longitudinal opposite left and right sides of said absorbent body on the side of a rear zone thereof.

9. A sanitary napkin according to claim 6, wherein said wing portion comprises a pair of left and right front wing portions disposed at longitudinal opposite left and right sides of said absorbent body on the side of a front zone thereof and a pair of left and right rear wing portions disposed at longitudinal opposite left and right sides of said absorbent body on the side of a rear zone thereof.

10. A sanitary napkin according to claim 7, wherein said sanitary napkin comprises an elongate upper layer portion comprised of a body absorbent core and a liquid-permeable topsheet disposed in such a manner as to cover upper and side surfaces of said body absorbent core; and a lower layer portion comprised of a liquid-impermeable antileakage sheet, a liquid-permeable sheet having a generally same configuration as said antileakage sheet and an absorptive sheet interposed between said liquid-impermeable antileakage sheet and said liquid-permeable sheet, said lower layer portion being enlarged in width dimension on the side of the front zone and the rear zone, said upper layer portion being placed on said liquid-permeable sheet of said lower layer portion such that the longitudinal opposite side portions of said lower layer portion, which are enlarged in width dimension, may extend from a longitudinal side edge of said upper layer portion, and, said front and rear wing portions being formed of said extended lower layer portion.

11. A sanitary napkin according to claim 8, wherein said sanitary napkin comprises an elongate upper layer portion comprised of a body absorbent core and a liquid-permeable topsheet disposed in such a manner as to cover upper and side surfaces of said body absorbent core; and a lower layer portion comprised of a liquid-impermeable antileakage sheet, a liquid-permeable sheet having a generally same configuration as said antileakage sheet and an absorptive sheet interposed between said liquid-impermeable antileakage sheet and said liquid-permeable sheet, said lower layer portion being enlarged in width dimension on the side of the front zone and the rear zone, said upper layer portion being placed on said liquid-permeable sheet of said lower layer portion such that the longitudinal opposite side portions of said lower layer portion, which are enlarged in width dimension, may extend from a longitudinal side edge of said upper layer portion, and, said front and rear wing portions being formed of said extended lower layer portion.

12. A sanitary napkin according to claim 9, wherein said sanitary napkin comprises an elongate upper layer portion comprised of a body absorbent core and a liquid-permeable topsheet disposed in such a manner as to cover upper and side surfaces of said body absorbent core; and a lower layer portion comprised of a liquid-impermeable antileakage sheet, a liquid-permeable sheet having a generally same configuration as said antileakage sheet and an absorptive sheet interposed between said liquid-impermeable antileakage sheet and said liquid-permeable sheet, said lower layer portion being enlarged in width dimension on the side of the front zone and the rear zone, said upper layer portion being placed on said liquid-permeable sheet of said lower layer portion such that the longitudinal opposite side portions of said lower layer portion, which are enlarged in width dimension, may extend from a longitudinal side edge of said upper layer portion, and, said front and rear wing portions being formed of said extended lower layer portion.

13. The sanitary napkin according to claim 1, wherein the thickness of each wing portion absorbent core is from 0.2 to 3 mm.

14. The sanitary napkin according to claim 1, wherein the thickness of each wing portion absorbent core is smaller than the thickness of said absorbent body.

* * * * *